US009265949B2

(12) United States Patent
Salo et al.

(10) Patent No.: US 9,265,949 B2
(45) Date of Patent: Feb. 23, 2016

(54) METHOD AND APPARATUS FOR CONTROLLING CARDIAC THERAPY BASED ON ELECTROMECHANICAL TIMING

(75) Inventors: Rodney Salo, Fridley, MN (US); Joseph M. Pastore, Woodbury, MN (US); Andrew P. Kramer, Stillwater, MN (US); Jeffrey E. Stahmann, Ramsey, MN (US); Jesse W. Hartley, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 3095 days.

(21) Appl. No.: 11/168,024

(22) Filed: Jun. 28, 2005

(65) Prior Publication Data

US 2006/0293714 A1    Dec. 28, 2006

(51) Int. Cl.
| | |
|---|---|
| *A61N 1/36* | (2006.01) |
| *A61N 1/362* | (2006.01) |
| *A61M 5/142* | (2006.01) |
| *A61N 1/365* | (2006.01) |
| *A61N 1/375* | (2006.01) |

(52) U.S. Cl.
CPC .......... *A61N 1/3627* (2013.01); *A61M 5/14276* (2013.01); *A61N 1/36585* (2013.01); *A61N 1/36521* (2013.01); *A61N 1/3756* (2013.01)

(58) Field of Classification Search
CPC ............................. A61N 1/3627; A61N 1/56
USPC .............. 607/4, 5, 9, 18, 62; 600/509, 513–5
See application file for complete search history.

(56) References Cited

U.S. PATENT DOCUMENTS

| | | |
|---|---|---|
| 3,995,623 A | 12/1976 | Blake et al. |
| 4,485,813 A | 12/1984 | Anderson et al. |
| 4,674,518 A | 6/1987 | Salo |
| 4,719,921 A | 1/1988 | Chirife |
| 4,773,401 A | 9/1988 | Citak et al. |
| 4,865,036 A | 9/1989 | Chirife |

(Continued)

OTHER PUBLICATIONS

Kim et al., Integrated MEMS for Pressure Transponder. *Transducers '97*, vol. 2, pp. 1011-1014. Jun. 16, 1997. 1997 International Conference on Solid-Stator Sensor and Actuators. Chicago, IL.

(Continued)

*Primary Examiner* — Theodore Stigell
*Assistant Examiner* — Natasha Patel
(74) *Attorney, Agent, or Firm* — Schwegman Lundberg & Woessner, P.A.

(57) ABSTRACT

Devices and methods for therapy control based on electromechanical timing involve detecting electrical activation of a patient's heart, and detecting mechanical cardiac activity resulting from the electrical activation. A timing relationship is determined between the electrical activation and the mechanical activity. A therapy is controlled based on the timing relationship. The therapy may improve intraventricular dyssynchrony of the patient's heart, or treat at least one of diastolic and systolic dysfunction and/or dyssynchrony of the patient's heart, for example. Electrical activation may be detected by sensing delivery of an electrical stimulation pulse to the heart or sensing intrinsic depolarization of the patient's heart. Mechanical activity may be detected by sensing heart sounds, a change in one or more of left ventricular impedance, ventricular pressure, right ventricular pressure, left atrial pressure, right atrial pressure, systemic arterial pressure and pulmonary artery pressure.

18 Claims, 5 Drawing Sheets

(56) References Cited

U.S. PATENT DOCUMENTS

| | | | |
|---|---|---|---|
| 5,083,563 A | 1/1992 | Collins | |
| 5,129,394 A | 7/1992 | Mehra | |
| 5,188,106 A * | 2/1993 | Nappholz et al. | 607/24 |
| 5,195,968 A | 3/1993 | Lundquist et al. | |
| 5,203,326 A * | 4/1993 | Collins | 607/4 |
| 5,324,326 A | 6/1994 | Lubin | |
| 5,334,222 A | 8/1994 | Salo et al. | |
| 5,389,090 A | 2/1995 | Fischell et al. | |
| 5,464,434 A | 11/1995 | Alt | |
| 5,584,868 A | 12/1996 | Salo et al. | |
| 5,674,256 A | 10/1997 | Carlson | |
| 5,700,283 A | 12/1997 | Salo | |
| 5,755,766 A | 5/1998 | Chastain et al. | |
| 6,059,778 A | 5/2000 | Sherman | |
| 6,066,126 A | 5/2000 | Li et al. | |
| 6,070,100 A * | 5/2000 | Bakels et al. | 607/9 |
| 6,096,036 A | 8/2000 | Bowe et al. | |
| 6,136,021 A | 10/2000 | Chastain et al. | |
| 6,198,952 B1 | 3/2001 | Miesel | |
| 6,198,974 B1 | 3/2001 | Webster, Jr. | |
| 6,221,011 B1 | 4/2001 | Bardy | |
| 6,237,398 B1 | 5/2001 | Porat et al. | |
| 6,270,457 B1 | 8/2001 | Bardy | |
| 6,270,496 B1 | 8/2001 | Bowe et al. | |
| 6,277,072 B1 | 8/2001 | Bardy | |
| 6,280,380 B1 | 8/2001 | Bardy | |
| 6,280,389 B1 | 8/2001 | Ding et al. | |
| 6,280,433 B1 | 8/2001 | McIvor et al. | |
| 6,309,350 B1 | 10/2001 | VanTassel et al. | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,398,738 B1 | 6/2002 | Millar | |
| 6,408,214 B1 | 6/2002 | Williams et al. | |
| 6,440,066 B1 | 8/2002 | Bardy | |
| 6,530,914 B1 | 3/2003 | Mickley | |
| 6,628,988 B2 * | 9/2003 | Kramer et al. | 607/9 |
| 6,666,826 B2 | 12/2003 | Salo et al. | |
| 6,853,861 B1 * | 2/2005 | Obel et al. | 607/27 |
| 7,164,948 B2 * | 1/2007 | Struble et al. | 607/22 |
| 2002/0040010 A1 | 4/2002 | Rosenzweig et al. | |
| 2002/0049478 A1 * | 4/2002 | Ding et al. | 607/17 |
| 2002/0107553 A1 | 8/2002 | Hill et al. | |
| 2003/0130581 A1 | 7/2003 | Salo | |
| 2005/0027323 A1 | 2/2005 | Mulligan et al. | |
| 2005/0043895 A1 | 2/2005 | Schechter | |
| 2006/0106322 A1 * | 5/2006 | Arand et al. | 600/514 |
| 2008/0287818 A1 * | 11/2008 | Shelchuk et al. | 600/509 |

OTHER PUBLICATIONS

File History for U.S. Appl. No. 10/745,031.
File History for EP Application No. 03701969.2 as retrieved from European Patent Office Electronic File System on Mar. 20, 2011, 136 pages.
File History for EP Application No. 06774332.8 as retrieved from European Patent Office Electronic File System on Mar. 20, 2011, 69 pages.
International Preliminary Report on Patentability dated Jan. 17, 2008 from PCT Application No. PCT/US2006/025524, 9 pages.
International Search Report dated Apr. 23, 2003 from PCT Application No. PCT/US03/00060, 8 pages.

* cited by examiner

METHOD AND APPARATUS FOR CONTROLLING CARDIAC THERAPY BASED ON ELECTROMECHANICAL TIMING

FIELD OF THE INVENTION

The present invention relates generally to a method and apparatus for cardiac pacing and, more particularly, to devices and methods for controlling cardiac therapy based on electromechanical timing.

BACKGROUND OF THE INVENTION

Heart disease (cardiomyopathy) can cause a patient to exhibit symptoms of congestive heart failure (CHF). CHF is a result of the weakening of the heart's cardiac function characterized by reduced pumping capacity and efficiency. Chronic cardiac rhythm problems can also be the result of cardiomyopathy. The modification of the heart's structure that causes the reduction in pumping capacity also causes modification of the heart's electrical characteristics. The heart's electrical pathways can become stretched out of shape and chemically damaged. This makes arrhythmias much more likely to occur in CHF patients.

Implantation of a pacemaker is a preferred method of treatment for arrhythmias in CHF patients. Although many types of heart problems may require a pacemaker, one method of treatment suited for CHF patients is known as cardiac resynchronization therapy (CRT). CRT uses a pacemaker with multiple pacing leads to coordinate the heart's chambers to act together in a sequence that will pump blood more efficiently.

It is likely that CRT candidates will have various forms of cardiomyopathy, and these patients may exhibit other measurable symptoms of reduced cardiac function besides arrhythmia. The reduced cardiac function of the heart is taken into account when applying CRT in order to tailor the treatment based on the needs of a particular patient. Various external factors must also be taken into account by the pacing system, one of those factors being the current state of activity of the patient.

Rate adaptive pacemakers are currently used that can estimate body activity by detecting body activity or breathing rate and depth, and therefore modify the pacing rate applied to the heart. These indicators can give a rough estimate of metabolic demand for a given patient. It would be beneficial to have more accurate measures of metabolic demand, especially measures that can determine the pumping capacity and pumping efficiency of a heart in order to measure and improve the efficacy of the therapy for the CHF patient.

SUMMARY OF THE INVENTION

The present invention is directed to a method and apparatus for cardiac pacing and, more particularly, to devices and methods for therapy control based on electromechanical timing. Methods in accordance with embodiments of the present invention involve detecting electrical activation of a patient's heart, and detecting mechanical cardiac activity resulting from the electrical activation. A timing relationship is determined between the detected electrical activation and the detected mechanical cardiac activity. A therapy delivered to the patient is controlled based on the timing relationship to treat dyssynchrony of the patient's heart.

For example, the therapy may be a therapy to improve intraventricular dyssynchrony of the patient's heart, or a therapy to treat at least one of diastolic and systolic dysfunction and/or dyssynchrony of the patient's heart. Electrical activation of the heart may be detected by sensing delivery of an electrical stimulation pulse to the heart or sensing intrinsic depolarization of the patient's heart, for example.

Mechanical cardiac activity may be detected by detecting a change in one or more of left ventricular pressure, right ventricular pressure, left atrial pressure, right atrial pressure, systemic arterial pressure and pulmonary artery pressure, indicative of mechanical cardiac activity resulting from the electrical activation, for example. Other embodiments involve detecting the mechanical cardiac activity by detecting a change in blood flow rate or blood perfusion and/or detecting ventricular motion or acceleration indicative of mechanical cardiac activity resulting from the electrical activation. Further methods of detecting the mechanical cardiac activity include transthoracically or intrathoracically detecting a change in ventricular impedance indicative of mechanical cardiac activity resulting from the electrical activation, and detecting heart sounds indicative of mechanical cardiac activity resulting from the electrical activation.

Other embodiments of methods in accordance with the present invention involve detecting electrical activation of a patient's heart using a patient-internal medical device, and detecting mechanical cardiac activity resulting from the electrical activation. A timing relationship is determined between the detected electrical activation and the detected mechanical cardiac activity. A therapy delivered to the patient is controlled based on the timing relationship. The therapy may be one or more of a cardiac pacing therapy, a CRT therapy, a ventricular assist therapy, a defibrillation therapy, a drug delivery therapy, a nerve stimulation therapy, and a ventricular remodeling reversal therapy, for example.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device in accordance with the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

A wide variety of implantable cardiac monitoring and/or stimulation devices may be configured to implement improved cardiac efficiency methodologies of the present invention. A non-limiting, representative list of such devices includes cardiac monitors, pacemakers, cardiovertors, defibrillators, resynchronizers, and other cardiac monitoring and therapy delivery devices. These devices may be configured with a variety of electrode arrangements, including transvenous, endocardial, and epicardial electrodes (i.e., intrathoracic electrodes), and may also include subcutaneous, non-intrathoracic electrodes, including can, header, and indifferent electrodes, and subcutaneous array or lead electrodes (i.e., non-intrathoracic electrodes).

Embodiments of the present invention may be implemented in the context of a wide variety of cardiac devices, such as those listed above, and are referred to herein generally as a patient-internal medical devices (PIMD) for convenience. A PIMD implemented in accordance with the present invention may incorporate one or more of the electrode and sensor types identified herein and/or incorporated herein by reference and/or combinations thereof.

Embodiments of the present invention are directed to devices and methods that use electrical and mechanical timing information to control the operation of a PIMD. The PIMD may also use the electrical and mechanical timing information subsequent to a change in therapy to assess the effectiveness of the therapy. The timing between electrical activity of the heart and the mechanical response of the myocardial tissue is denoted as the electromechanical timing (EMT). The time-period between the electrical stimulation of the myocardial tissue and the mechanical response (e.g. contraction) of the myocardial tissue is denoted as the electromechanical delay (EMD). EMT is a function of sympathetic and parasympathetic balance, as well as the efficiency of the mechanical activation.

The mechanical response of the myocardial tissue may be determined using implantable and/or external sensors. Examples of suitable sensors include pressure sensors, impedance sensors, blood-flow sensors, acoustic sensors, and motion and/or acceleration sensors.

The electrical timing may be established using the timing of stimulation pulses from a PIMD and/or the measured evoked and/or intrinsic electrical activity. EMT/EMD information may be used to initiate, change, and/or titrate therapies for PIMDs, such as intra and/or inter-ventricular delays, atrio-ventricular (AV) delay, pacing therapy, ventricular assist device control, as well as therapies such as neural stimulation, cardiac resynchronization therapy, defibrillation therapy, drug delivery therapy, and ventricular remodeling reversal therapy, for example.

In embodiments of the present invention, the use of EMT/EMD to control therapy may be performed periodically, regularly, or continuously. In other embodiments of the present invention, the use of EMT/EMD to control therapy may be performed only on command, such as from a patient-external device, or only upon existence of a predetermined condition and/or state of the PIMD. It may be desirable to only use mechanical sensors that consume significant energy sparingly, to conserve energy. In other embodiments, the EMT/EMD may be determined using sensors, such as transthoracic impedance sensors, without incremental energy loss from the sensor. For example, the sensor may be patient-external, such as a wearable sensor, that may have an independent power source.

One example of a device that may benefit from EMT/EMD control in accordance with the present invention is a rate adaptive pacing system that may be controlled to increase rate during decreased EMD. In another example, a cardiac resynchronization therapy (CRT) system may use EMT/EMD information to minimize EMD during patient rest periods, thereby maximizing synchrony of the heart. In a further example, a sudden change in EMD along with increase in heart rate may be used to confirm a ventricular tachycardia. Further, a sudden increase in EMD may indicate a loss of capture, and initiate a capture threshold algorithm, for example. EMT/EMD information may also be useful to monitor a patient's left heart/global function, including contractility and intracardiac synchrony, as another example.

EMT/EMD measurement for PIMD control in accordance with the present invention is applicable to patients receiving therapy for inter or intraventricular dyssynchrony. This includes patients currently indicated for CRT as well as patients with diastolic dysfunction and dyssynchrony, as well as post myocardial infarction (MI) patients undergoing remodeling control therapy.

A particular embodiment in accordance with the present invention involves measuring the time interval between paced or intrinsic electrical activation of the left ventricle, and the beginning of global mechanical activation as measured by an increase in the impedance between a coronary vein electrode on the lateral wall and an electrode in either the right ventricle or right atrium.

In a patient with dyssynchronous contraction and relaxation of the heart (e.g. patients undergoing CRT therapy), the EMD shortens as the activation of the ventricle becomes more synchronous. Under resting or other steady-state conditions, therapy parameters may be varied to search for the combination that results in the shortest (or shortened) EMD. The EMD may also be monitored to assess the worsening or improving cardiac dyssynchrony of the patient. This information may be recorded locally, or transmitted via telemetry to a patient-external device, as will be further described below.

Figure 1A:
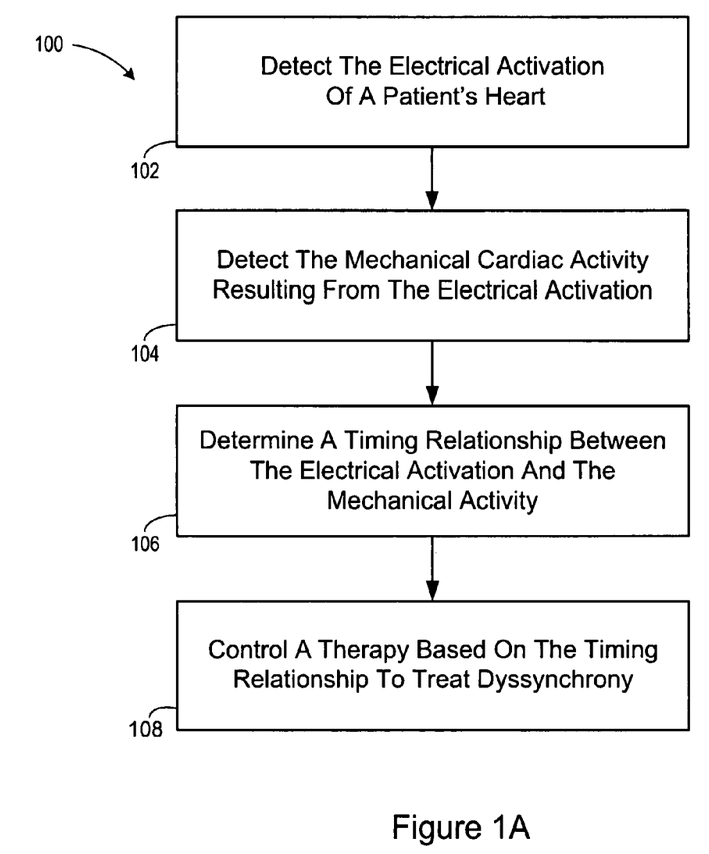
FIG. 1A is a flow chart of a method of therapy control using electromechanical timing information in accordance with the present invention.

FIG. 1A is a flow chart of a method 100 of therapy control to treat dyssynchrony of a patient's heart using electromechanical timing information in accordance with the present invention. The method 100 involves detecting 102 electrical activation of a patient's heart, and detecting 104 mechanical cardiac activity resulting from the electrical activation. A timing relationship is determined 106 between the detected electrical activation 102 and the detected mechanical cardiac activity 104. A therapy delivered to the patient is controlled 108 based on the timing relationship to treat dyssynchrony of the patient's heart.

For example, the therapy may be a therapy to improve intraventricular dyssynchrony of the patient's heart, or a therapy to treat at least one of diastolic and systolic dysfunction and/or dyssynchrony of the patient's heart. Electrical activation of the heart may be detected 102 by sensing delivery of an electrical stimulation pulse to the heart or sensing intrinsic depolarization of the patient's heart.

Mechanical cardiac activity may be detected 104 by detecting a change in at least one of left ventricular pressure, right ventricular pressure, left atrial pressure, right atrial pressure, systemic arterial pressure and pulmonary artery pressure, indicative of mechanical cardiac activity resulting from the electrical activation, for example. Detecting 104 the mechanical cardiac activity may also be done by transthoracically or intrathoracically detecting a change in ventricular impedance indicative of mechanical cardiac activity resulting from the electrical activation, or by detecting heart sounds indicative of mechanical cardiac activity resulting from the electrical activation. Other ways of detecting 104 the mechanical cardiac activity include detecting a change in blood flow rate or blood perfusion and/or detecting ventricular motion or acceleration indicative of mechanical cardiac activity resulting from the electrical activation.

Figure 1B:
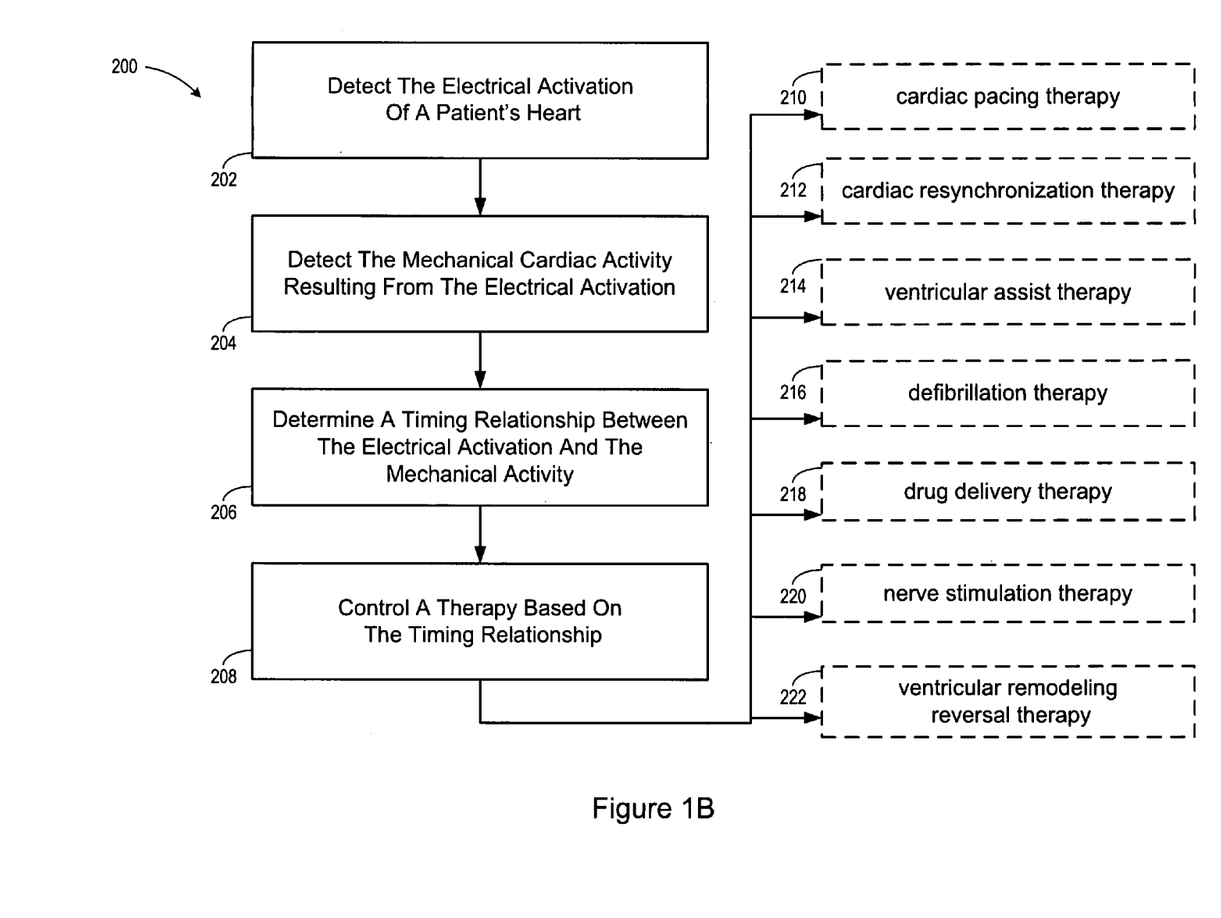
FIG. 1B is a flow chart of another method of therapy control using electromechanical timing information in accordance with the present invention.

FIG. 1B is a flow chart of a method 200 of therapy control using electromechanical timing information in accordance with the present invention. The method 200 involves detecting electrical activation 202 of a patient's heart using a patient-internal medical device, and detecting mechanical cardiac activity 204 resulting from the electrical activation. A timing relationship is determined 206 between the detected electrical activation 202 and the detected mechanical cardiac activity 204. A therapy delivered to the patient is controlled 208 based on the timing relationship. The therapy may be one or more of a cardiac pacing therapy 210, a CRT therapy 212, a ventricular assist therapy 214, a defibrillation therapy 216, a drug delivery therapy 218, a nerve stimulation therapy 220, and a ventricular remodeling reversal therapy 222, for example.

Ventricular assist therapy 214 may include a left ventricular assist device (LAVD) that either takes over or assists the pumping role of the left ventricle, the heart's main pumping chamber. LVADs may be permanent in people with severe heart failure. In an LAVD, part of the device is implanted in a patient's heart and abdomen, and part remains outside the body. The external part of the device may be carried on a belt around the patient's waist or on a shoulder strap. Typically, LVADs have an electric pump, an electronic controller, an energy supply (usually a battery weighing about 8 pounds) and 2 tubes. One tube carries blood from the left ventricle into the device. The other tube takes blood pumped from the device into the aorta (artery) to be circulated throughout the body.

LVADs are used to "unload" the heart (by taking over some of the pumping activity) to allow it to recover from some injury, or to assist for patients with chronic heart failure (CHF). The electromechanical timing in accordance with the present invention may be used to control the degree of unloading that takes place, and permits the heart to handle more load as it recovers, or less load if a relapse occurs.

Drug delivery therapy 218 may include a drug-delivery system for local delivery of inotropes, Angiotensin II receptor blockers (ARBs), or other drugs through cardiac veins to control contractility. This system may use feedback control via electromechanical interval measurement in accordance with the present invention.

Nerve stimulation therapy 220 may be performed using a Vagus nerve stimulator that reduces contractility in the context of hypertension or cardiac injury, for example. Nerve stimulation therapy 220 may be used to retard or prevent adverse remodeling. Feedback (via EMT/EMD) may be used in accordance with the present invention to maintain the desired degree of therapy during daily activities such as exercise, sleep, etc.

Detecting mechanical cardiac activity 204 resulting from the electrical activation may be done using a subcutaneous sensor, such as an accelerometer or acoustic transducer, which may be used to detect heart sounds as will be described in more detail below. The heart sounds may be used to determine EMD information and timing in accordance with the present invention. A PIMD device may utilize one or more of the presence, characteristics, and frequency of occurrence of the heart sound combined with ECG information when determining EMT and EMD.

A heart rate determined from the ECG signal may, for example, be analyzed along with heart sound information. It should also be noted that other sensor-derived signals could replace heart sounds. For example, impedance, pulse pressure, blood volume/flow, or cardiac accelerations could be used.

Various types of acoustic sensors may be used to detect heart sounds. Examples of such acoustic sensors include diaphragm based acoustic sensors, MEMS-based acoustic sensors such as a MEMS-based acoustic transducer, fiber optic acoustic sensors, piezoelectric sensors, and accelerometer based acoustic sensors and arrays. These sensors may be used to detect the audio frequency pressure waves associated with the heart sounds, and may also be used to detect other non-electrophysiologic cardiac related signals.

Figure 2:
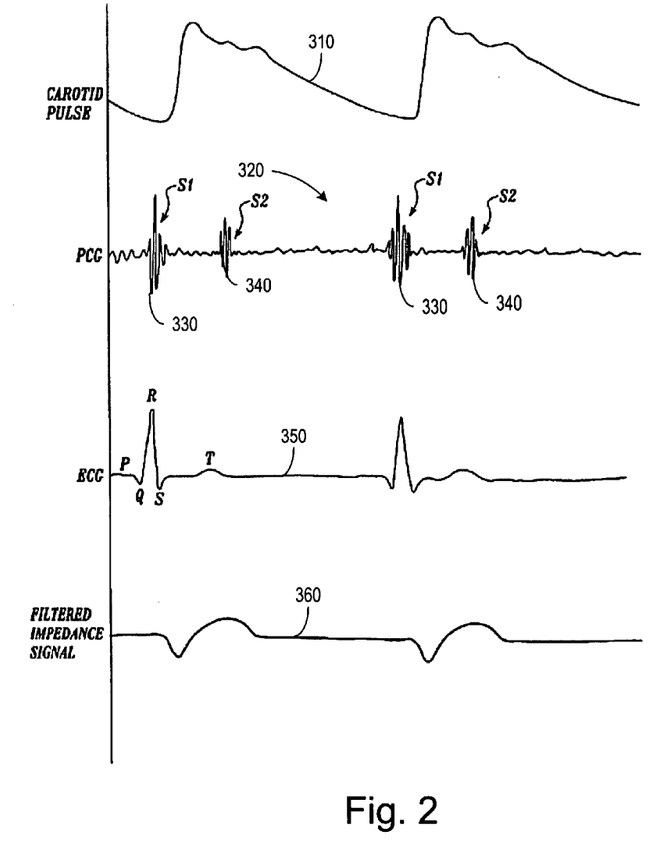
FIG. 2 is a pictorial diagram of a carotid pulse waveform, a phonocardiogram (PCG) waveform, an electrocardiogram (ECG) waveform, and a filtered transthoracic impedance signal for two consecutive heartbeats.

The presence of cardiac pulse, or heartbeat, in a patient is generally detected by palpating the patient's neck and sensing changes in the volume of the patient's carotid artery due to blood pumped from the patient's heart. A graph of a carotid pulse signal 310, representative of the physical expansion and contraction of a patient's carotid artery during two consecutive pulses, or heartbeats, is shown at the top of FIG. 2. When the heart's ventricles contract during a heartbeat, a pressure wave is sent throughout the patient's peripheral circulation system. The carotid pulse signal 310 shown in FIG. 2 rises with the ventricular ejection of blood at systole and peaks when the pressure wave from the heart reaches a maximum. The carotid pulse signal 310 falls off again as the pressure subsides toward the end of each pulse.

The opening and closing of the patient's heart valves during a heartbeat causes high-frequency vibrations in the adjacent heart wall and blood vessels. These vibrations can be heard in the patient's body as heart sounds, and may be detected by sensors, as described earlier. A conventional phonocardiogram (PCG) transducer placed on a patient converts the acoustical energy of the heart sounds to electrical energy, resulting in a PCG waveform 320 that may be recorded and displayed, as shown by the graph in the upper middle portion of FIG. 2.

As indicated by the PCG waveform 320 shown in FIG. 2, a typical heartbeat produces two main heart sounds. A first heart sound 330, denoted S1, is generated by vibration generally associated with the closure of the tricuspid and mitral valves at the beginning of systole. Typically, the heart sound 330 is about 14 milliseconds long and contains frequencies up to approximately 500 Hz. A second heart sound 340, denoted S2, is generally associated with vibrations resulting from the closure of the aortic and pulmonary valves at the end of systole. While the duration of the second heart sound 340 is typically shorter than the first heart sound 330, the spectral bandwidth of the second heart sound 340 is typically larger than that of the first heart sound 330.

An electrocardiogram (ECG) waveform 350 describes the electrical activity of a patient's heart. The graph in the lower middle portion of FIG. 2 illustrates an example of the ECG waveform 350 for two heartbeats and corresponds in time with the carotid pulse signal 310 and PCG waveform 320 also shown in FIG. 2. Referring to the first shown heartbeat, the portion of the ECG waveform 350 representing depolarization of the atrial muscle fibers is referred to as the "P" wave. Depolarization of the ventricular muscle fibers is collectively represented by the "Q," "R," and "S" waves of the ECG waveform, referred to as the QRS complex. Finally, the portion of the waveform representing repolarization of the ventricular muscle fibers is known as the "T" wave. Between heartbeats, the ECG waveform 350 returns to an isopotential level.

Fluctuations in a patient's transthoracic impedance signal 360 also correlate with the patients electromechanical timing and EMD. The bottom graph of FIG. 2 illustrates an example of a filtered transthoracic impedance signal 360 for a patient in which fluctuations in impedance correspond in time with the carotid pulse signal 310, the PCG waveform 320, and ECG waveform 350, also shown in FIG. 2. Impedance signals that may be useful in accordance with the present invention include transthoracic impedance, measured between the PIMD housing and an electrode, or may include local impedance measurements from implanted electrodes, such as bi-polar electrodes, for example.

Given that EMD information can be a useful indicator of heart performance, the EMD information can be beneficially applied to adaptively change therapy parameters, for example, of a cardiac pacing or defibrillation system. Further, analyzing EMD information can provide a pacing system with the ability to measure and adapt to heart activity over a long period of time in order to measure and improve the efficacy of the pacing treatment for the CHF patient.

Figure 3:
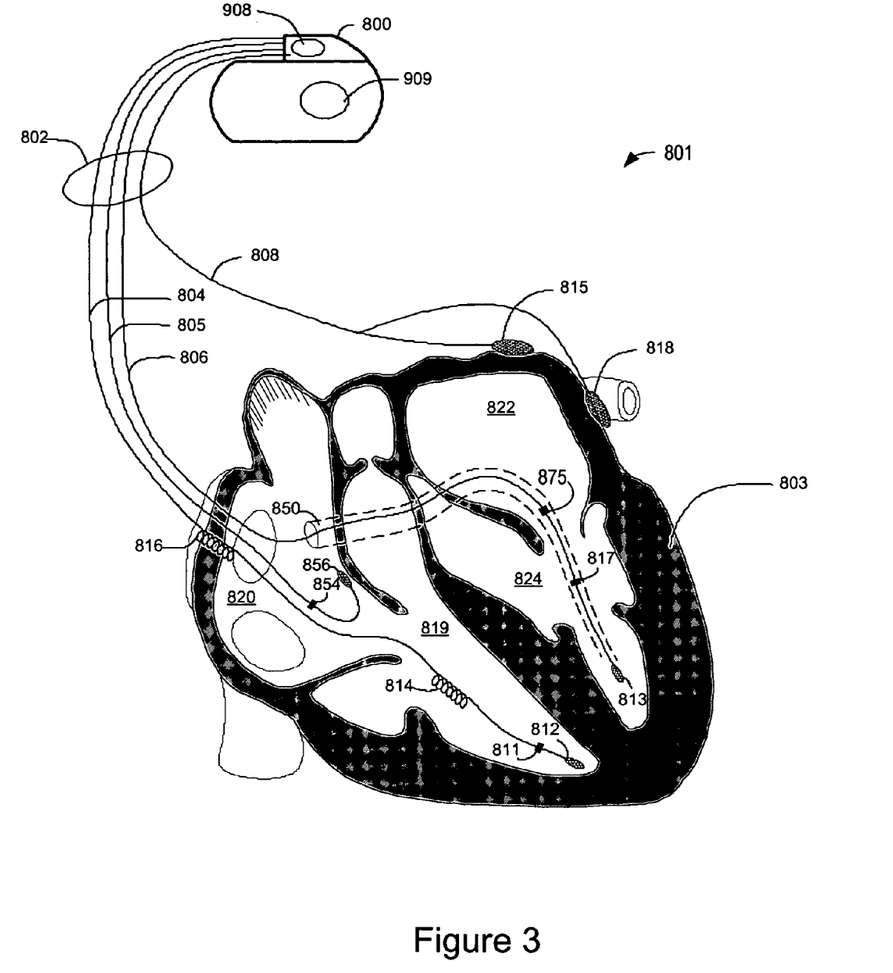
FIG. 3 is a view of the heart showing an apparatus in accordance with the present invention illustrating a lead system implanted in the heart.

Turning now to FIG. 3, a system in accordance with the present invention is shown having a lead system deployed within a heart. A PIMD system 801 includes a PIMD 800 with a lead system 802 that is designed for implantation in a coronary vein for purposes of CRT. The lead system 802 is coupled to a detection/energy delivery system 900 (Illustrated in FIG. 4) that actively measures and controls the implanted lead system to provide cardiac pacing therapy to a patient's heart 803.

The detector/energy delivery system 900 typically includes a power supply and programmable circuit (e.g., microprocessor) coupled to an analog to digital (A-D) converter. Various lead system devices, such as electrodes and pressure sensors, can interface to the A-D converter for sensing/data collection. Alternatively, analog conditioning (e.g., filtering) may be applied to sensor signals before interfacing with the A-D converter. The detector/energy delivery system 900 also utilizes an energy delivery system. The energy delivery system may include charge capacitors and signal conditioning circuitry known in the art. The energy system may interface to the programmable circuit through a D-A converter. Components and functionality of the detector/energy delivery system 900 will be further described below with reference to FIG. 4.

Still referring to FIG. 3, the lead system 802 may be implanted into the coronary sinus using various techniques. One such technique, as illustrated in FIG. 3, involves creating an opening in a percutaneous access vessel such as the left subclavian or left cephalic vein. The pacing lead is guided into a right atrial chamber 820 of the heart via the superior vena cava. From the right atrial chamber 820, the lead system 802 is sent into the coronary sinus ostium. The ostium is the opening of a coronary sinus 850 into the right atrial chamber 820. The lead system 802 is guided through the coronary sinus 850 to a coronary vein of the left ventricle 824. A distal end of the lead system 802 may be lodged into the coronary vein.

The PIMD system 801 may be used to implement methods for therapy control based on electromechanical timing in accordance with the present invention. The PIMD system 801 in FIG. 3 is illustrated having the PIMD 800 electrically and physically coupled to the lead system 802. The housing and/or header of the PIMD 800 may incorporate one or more electrodes 908, 909 used to provide electrical stimulation energy to the heart and to sense cardiac electrical activity. The PIMD 800 may utilize all or a portion of the PIMD housing as a can electrode 909. The PIMD 800 may include an indifferent electrode positioned, for example, on the header or the housing of the PIMD 800. If the PIMD 800 includes both a can electrode 909 and an indifferent electrode 908, the electrodes 908, 909 typically are electrically isolated from each other.

The lead system 802 is used to provide pacing signals to the heart 803, detect electric cardiac signals produced by the heart 803, sense blood oxygen saturation, and may also be used to provide electrical energy to the heart 803 under certain predetermined conditions to treat cardiac arrhythmias. The lead system 802 may include one or more electrodes used for pacing, sensing, and/or defibrillation. In the embodiment shown in FIG. 3, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 3 illustrates one embodiment that may be used in connection with therapy control based on electromechanical timing methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 803. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 3, the lead system 802 may include one or more extracardiac leads 808 having electrodes, e.g., epicardial electrodes or sensors 815, 818, positioned at locations outside the heart for sensing and/or pacing one or more heart chambers.

The right ventricular lead system 804 illustrated in FIG. 3 includes an SVC-coil 816, an RV-coil 814, an RV-ring electrode 812, and an RV-tip electrode 811. The right ventricular lead system 804 extends through the right atrium 820 and into the right ventricle 819. In particular, the RV-tip electrode 811, RV-ring electrode 812, and RV-coil electrode 814 are positioned at appropriate locations within the right ventricle 819 for sensing and delivering electrical stimulation pulses to the heart. The SVC-coil 816 is positioned at an appropriate location within the right atrium chamber 820 of the heart 803 or a major vein leading to the right atrial chamber 820 of the heart 803.

In one configuration, the RV-tip electrode 811 referenced to the can electrode 909 may be used to implement unipolar pacing and/or sensing in the right ventricle 819. Bipolar pacing and/or sensing in the right ventricle may be implemented using the RV-tip 811 and RV-ring 812 electrodes. In yet another configuration, the RV-ring 812 electrode may optionally be omitted, and bipolar pacing and/or sensing may be accomplished using the RV-tip electrode 811 and the RV-coil 814, for example. The right ventricular lead system 804 may be configured as an integrated bipolar pace/shock lead. The RV-coil 814 and the SVC-coil 816 are defibrillation electrodes.

The left ventricular lead 806 includes an LV distal electrode 817 and an LV proximal electrode 813 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart, and to sense blood oxygen levels in the blood leaving the myocardium. Lead placement for the left ventricular lead 806 may be achieved via subclavian vein access and a preformed guiding catheter for insertion of the LV electrodes 817, 813 adjacent to the left ventricle.

Unipolar pacing and/or sensing in the left ventricle may be implemented, for example, using the LV distal electrode referenced to the can electrode 909. The LV distal electrode 817 and the LV proximal electrode 813 may be used together as bipolar sense and/or pace electrodes for the left ventricle. The left ventricular lead 806 and the right ventricular lead 804, in conjunction with the PIMD 800, may be used to provide cardiac resynchronization therapy such that the ventricles of the heart are paced substantially simultaneously, or in phased sequence, to provide enhanced cardiac pumping efficiency in accordance with the present invention for patients suffering from chronic heart failure.

The right atrial lead 805 includes a RA-tip electrode 854 and an RA-ring electrode 856 positioned at appropriate locations in the right atrium 820 for sensing and pacing the right atrium 820. In one configuration, the RA-tip 854 referenced to the can electrode 909, for example, may be used to provide unipolar pacing and/or sensing in the right atrium 820. In another configuration, the RA-tip electrode 854 and the RA-ring electrode 856 may be used to provide bipolar pacing and/or sensing.

The left ventricular lead 806, as shown in FIG. 3, may include a pressure transducer 875. The pressure transducer 875 used in this application can be a micro-electrical-mechanical system (MEMS), for example. MEMS technology uses semiconductor techniques to build microscopic mechanical devices in silicon or similar materials. The pressure transducer 875 can include a micromachined capacitive or piezoresistive transducer exposed to the bloodstream. Other pressure transducer technologies, such as resistive strain gages, are known in the art and can also be employed as a pressure transducer 875. The pressure transducer 875 is coupled to one or more conductors disposed along the length of the left ventricular lead 806. In the configuration shown in FIG. 3, the pressure transducer 875 is integrated with the left ventricular lead 806. Transducers such as the pressure transducer 875 may be used to determine pulmonary arterial (PA) pressure information useful for determining EMD information in accordance with the present invention. Pressure sensor devices and methodologies are further described in U.S. Pat. No. 6,237,398, which is hereby incorporated herein by reference.

Figure 4:
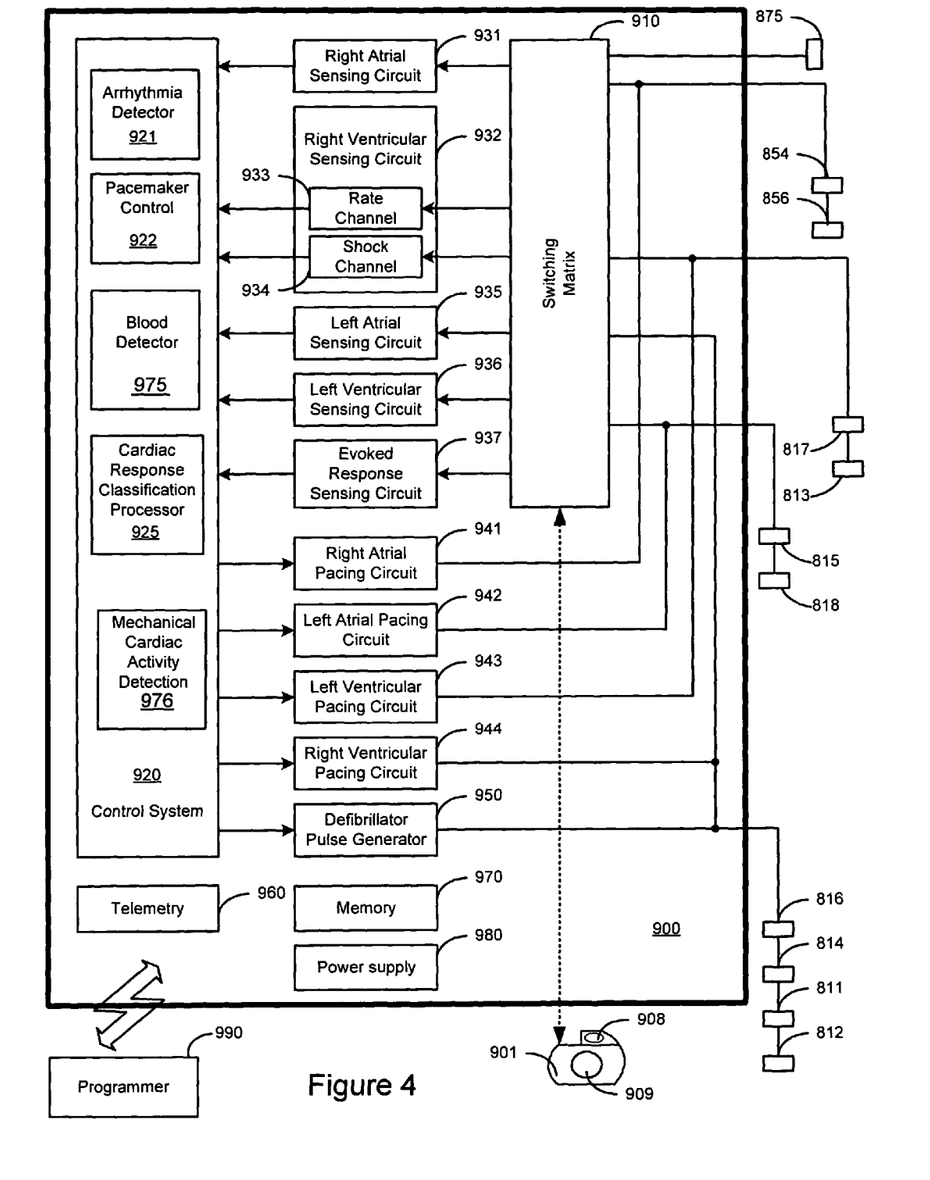
FIG. 4 is a block diagram of a system in accordance with the present invention.

Referring now to FIG. 4, there is shown an embodiment of a PIMD 900 suitable for therapy control based on electromechanical timing in accordance with the present invention. FIG. 4 shows the PIMD 900 divided into functional blocks. It is understood by those skilled in the art that there exist many possible configurations in which these functional blocks can be arranged. The example depicted in FIG. 4 is one possible functional arrangement. Other arrangements are also possible. For example, more, fewer or different functional blocks may be used to describe a PIMD suitable for implementing the methodologies for adaptive windowing in accordance with the present invention. In addition, although the PIMD 900 depicted in FIG. 4 contemplates the use of a programmable microprocessor-based logic circuit, other circuit implementations may be utilized.

The PIMD 900 depicted in FIG. 4 includes circuitry for receiving cardiac signals from a heart and delivering electrical stimulation energy to the heart in the form of pacing pulses and/or defibrillation shocks. In one embodiment, the circuitry of the PIMD 900 is encased and hermetically sealed in a housing 901 suitable for implanting in a human body. Power to the PIMD 900 is supplied by an electrochemical battery 980. A connector block (not shown) is attached to the housing 901 of the PIMD 900 to allow for the physical and electrical attachment of the lead system conductors to the circuitry of the PIMD 900.

The PIMD 900 may be a programmable microprocessor-based system, including a controller 920 and a memory 970. The memory 970 may store parameters for various pacing, defibrillation, and sensing modes, along with other parameters. Further, the memory 970 may store data indicative of signals received by other components of the PIMD 900. The memory 970 may be used, for example, for storing historical EMT/EMD information, blood oxygen levels, blood flow information, perfusion information, heart sounds, heart movement, EGM, and/or therapy data. The historical data storage may include, for example, data obtained from long-term patient monitoring used for trending or other diagnostic purposes. Historical data, as well as other information, may be transmitted to an external programmer unit 990 as needed or desired.

The controller 920 and memory 970 may cooperate with other components of the PIMD 900 to control the operations of the PIMD 900. The control system depicted in FIG. 4 incorporates a processor 925 for classifying cardiac responses to pacing stimulation. The controller 920 may include additional functional components including a pacemaker control circuit 922, an arrhythmia detector 921, and a template processor for cardiac signal morphology analysis, along with other components for controlling the operations of the PIMD 900. The controller 920 may include blood detector circuitry 975 configured to determine blood perfusion, blood flow, and/or blood pressure based on one or more sensors. The controller 920 may optionally, or additionally, include mechanical cardiac activity detection circuitry 976 configured to detect mechanical cardiac activity using sensor information from, for example, an accelerometer, a microphone, a pressure transducer, impedance sensors, or other motion or sound sensing arrangements.

Telemetry circuitry 960 may be implemented to provide communications between the PIMD 900 and an external programmer unit 990. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the controller 920 of the PIMD 900 from the programmer unit 990 during and after implant. In addition, stored cardiac data pertaining to EMT/EMD, capture threshold, capture detection and/or cardiac response classification, for example, along with other data, may be transferred to the programmer unit 990 from the PIMD 900.

The telemetry circuitry 960 may also allow the PIMD device to communicate with one or more receiving devices or systems situated external to the PIMD device. By way of example, the PIMD device may communicate with a patient-worn, portable or bedside communication system via the telemetry circuitry 960. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the PIMD device via the telemetry circuitry 960. It is noted that physiologic or non-physiologic sensors equipped with wireless transmitters or transceivers may communicate with a receiving system external of the patient. The external sensors in communication with the PIMD may be used to determine electromechanical timing and/or delays in accordance with embodiments of the present invention.

In the embodiment of the PIMD 900 illustrated in FIG. 3, electrodes RA-tip 854, RA-ring 856, RV-tip 811, RV-ring 812, RV-coil 814, SVC-coil 816, LV distal electrode 817, LV proximal electrode 813, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 854 and the RA-ring 856. Unipolar sensing may be implemented, for example, by sensing voltages developed between the RA-tip 854 and the can electrode 909. Outputs from the right atrial sensing circuit are coupled to the controller 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 811 electrode are right ventricular near-field signals and are denoted RV rate channel signals. A bipolar RV rate channel signal may be sensed as a voltage developed between the RV-tip 811 and the RV-ring 812. Alternatively, bipolar sensing in the right ventricle may be implemented using the RV-tip electrode 811 and the RV-coil 814. Unipolar rate channel sensing in the right ventricle may be implemented, for example, by sensing voltages developed between the RV-tip 811 and the can electrode 909.

Right ventricular cardiac signals sensed through use of the RV-coil electrode 814 are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration the can electrode 909 and the SVC-coil electrode 816 may be electrically shorted and a RV shock channel signal may be detected as the voltage developed between the RV-coil 814 and the can electrode 909/SVC-coil 816 combination.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

Referring still to FIG. 4, a left ventricular sensing circuit 936 serves to detect and amplify electrical signals from the left ventricle of the heart. Bipolar sensing in the left ventricle may be implemented, for example, by sensing voltages developed between the LV distal electrode 817 and the LV proximal electrode 813. Unipolar sensing may be implemented, for example, by sensing voltages developed between the LV distal electrode 817 or the LV proximal electrode 813 and the can electrode 909.

Optionally, an LV coil electrode (not shown) may be inserted into the patient's cardiac vasculature, e.g., the coronary sinus, adjacent the left heart. Signals detected using combinations of the LV electrodes, 817, 813, LV coil electrode (not shown), and/or can electrodes 909 may be sensed and amplified by the left ventricular sensing circuitry 936. The output of the left ventricular sensing circuit 936 is coupled to the controller 920.

Measuring LVP may be useful in accordance with the present invention to measure the EMD. For example, in cardiac therapy using bi-ventricular pacing (e.g., CRT), benefits are obtained from synchronizing the contractions of the right and left ventricle using pacing electrodes. If a method or apparatus for acquiring a right ventricular pressure (RVP) signal is provided (for example, via a pressure transducer incorporated into a right ventricular pacing lead) and the left ventricular pressure signal is acquired from a coronary venous lead, the degree of synchronization of these two chambers can be assessed by plotting RVP versus the LVP and determining the area of the resulting approximately elliptical shape. This elliptical shape is referred to as a PP Loop. Methods and systems for measuring the left ventricular pressure are further described in U.S. Pat. No. 6,666,826, which is hereby incorporated herein by reference.

A method and apparatus for using the PP Loop for characterizing therapy for CHF patients is described in commonly owned U.S. Pat. No. 6,280,389, which is hereby incorporated herein by reference. A given parameter (e.g., atrioventricular delay or interventricular delay) associated with CRT may be optimized by varying the parameter(s) to minimize the PP Loop area. This process can be carried out periodically to correct for physiological changes that may occur in the course of the disease or therapy. The relative timing or phase of these pressure signals may be extracted by analysis of maximum or minimum threshold values from time domain pressure readings. Relative phasing can also be determined from the frequency domain by analyzing the fundamental of a Fourier analysis, such as by use of a Fast Fourier Transform (e.g., FFT) analysis. The computation required to perform FFT and/or extract timing values from pressure signals is known in the art and can be readily implemented in the controller.

Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of treating dyssynchrony of a patient's heart, comprising:
   detecting electrical depolarization of a patient's ventricular tissue;
   detecting mechanical cardiac activity of the ventricular tissue resulting from the electrical depolarization;
   determining a timing relationship between the detected electrical depolarization and the detected mechanical cardiac activity; and
   controlling a therapy delivered to the patient based on the timing relationship to treat at least one of intraventricular dyssynchrony and dyssynchrony between the left and right ventricles, wherein at least one of the steps of determining and controlling is implemented at least in part by a circuit.

2. The method of claim 1, wherein the detected mechanical cardiac activity comprises at least one of contraction and relaxation of the patient's heart.

3. The method of claim 1, wherein the therapy comprises a therapy to improve interventricular dyssynchrony of the patient's heart.

4. The method of claim 1, wherein the therapy comprises a therapy to treat at least one of diastolic and systolic dysfunction of the patient's heart.

5. The method of claim 1, wherein the therapy comprises a therapy to treat at least one of diastolic and systolic dyssynchrony.

6. The method of claim 1, wherein the therapy comprises a ventricular remodeling reversal therapy.

7. The method of claim 1, wherein the therapy comprises a therapy to improve dyssynchrony between the left and right ventricles.

8. The method of claim 1, wherein detecting the mechanical cardiac activity comprises detecting a change in at least one of left ventricular pressure, right ventricular pressure, left atrial pressure, right atrial pressure, systemic arterial pressure and pulmonary artery pressure, indicative of mechanical cardiac activity resulting from the electrical depolarization.

9. The method of claim 1, wherein detecting the mechanical cardiac activity comprises transthoracically or intrathoracically detecting a change in ventricular impedance indicative of mechanical cardiac activity resulting from the electrical depolarization.

10. The method of claim 1, wherein detecting the mechanical cardiac activity comprises detecting heart sounds indicative of mechanical cardiac activity resulting from the electrical depolarization.

11. The method of claim 1, wherein detecting the mechanical cardiac activity comprises detecting a change in blood flow rate or blood perfusion indicative of mechanical cardiac activity resulting from the electrical depolarization.

12. The method of claim 1, wherein detecting the mechanical cardiac activity comprises detecting ventricular motion or acceleration indicative of mechanical cardiac activity resulting from the electrical depolarization.

13. The method of claim 1, wherein each of detecting electrical depolarization and detecting mechanical cardiac activity is performed patient-internally.

14. The method of claim 1, wherein the electrical depolarization of the patient's ventricular tissue is evoked by a pace pulse.

15. The method of claim 1, wherein the electrical depolarization of the patient's ventricular tissue is caused by intrinsic electrical activation of the patient's heart.

16. The method of claim 1, wherein controlling the therapy delivered to the patient comprises controlling the therapy to reduce a time interval between the detected electrical depolarization and the detected mechanical cardiac activity.

17. The method of claim 1, further comprising performing a capture test and detecting capture using the timing relationship.

18. An implantable cardiac device, comprising:
   means for detecting electrical depolarization of a patient's ventricular tissue;
   means for detecting mechanical cardiac activity of the ventricular tissue resulting from the electrical depolarization;
   means for determining a timing relationship between the detected electrical depolarization and the detected mechanical cardiac activity; and
   means for controlling a therapy delivered to the patient based on the timing relationship to treat at least one of intraventricular dyssynchrony and dyssynchrony between the left and right ventricles.

* * * * *